United States Patent
Tanaka et al.

(10) Patent No.: US 7,157,609 B2
(45) Date of Patent: Jan. 2, 2007

(54) PROCESS FOR PRODUCING PROPYLENE CHLOROHYDRIN

(75) Inventors: Hiroki Tanaka, Tokuyama (JP); Yoji Mizushima, Tokuyama (JP); Yoshikazu Kodama, Tokuyama (JP); Tomoaki Fujii, Tokuyama (JP); Manabu Kamamoto, Tokuyama (JP); Koujiro Miyazaki, Tokuyama (JP)

(73) Assignee: Tokuyama Corporation, Tokuyama (JP)

( * ) Notice: Subject to any disclaimer, the term of this patent is extended or adjusted under 35 U.S.C. 154(b) by 587 days.

(21) Appl. No.: 10/442,282

(22) Filed: May 21, 2003

(65) Prior Publication Data

US 2004/0030198 A1 Feb. 12, 2004

Related U.S. Application Data

(60) Provisional application No. 60/381,917, filed on May 21, 2002.

(51) Int. Cl.
- *C07C 29/00* (2006.01)
- *C07C 31/34* (2006.01)
- *C07C 31/30* (2006.01)

(52) U.S. Cl. .................. 568/850; 568/841; 568/851

(58) Field of Classification Search .............. 568/841, 568/850, 851

See application file for complete search history.

(56) References Cited

FOREIGN PATENT DOCUMENTS

| CN | 1232011 A | 10/1999 |
|---|---|---|
| JP | 2553261 B2 | 8/1996 |
| JP | 2001-335520 A | 4/2001 |
| JP | 2002-154999 A | 5/2002 |
| WO | WO 96/00709 A1 | 1/1996 |

OTHER PUBLICATIONS

Nikkan Kogyo Gisensyo 14, pp. 106-119, Nov. 25, 1962, with English translation of pp. 106-110.

*Primary Examiner*—J. Parsa
(74) *Attorney, Agent, or Firm*—Birch, Stewart, Kolasch & Birch, LLP

(57) ABSTRACT

A process of producing propylene chlorohydrin using a reactor having a one-way flow reaction area and a circulating flow reaction area which are connected in series. In this process, a propylene-containing gas is supplied to an aqueous solution of chlorine in the one-way flow reaction area to carry out at least part of a propylene chlorohydrin forming reaction so as to form a reaction mixture fluid containing propylene chlorohydrin and propylene and/or chlorine. The above reaction mixture fluid discharged from this reaction area is supplied to the circulating flow reaction area as at least part of a make-up medium, a propylene-containing gas and/or chlorine are/is supplied as required to continue the reaction in the circulating flow reaction area so as to obtain a reaction solution having a desired content of propylene chlorohydrin, and part of the reaction solution is extracted.

6 Claims, 3 Drawing Sheets

PROCESS FOR PRODUCING PROPYLENE CHLOROHYDRIN

This application claims priority on Provisional Application No. 60/381,917 filed May 21, 2002, the entire contents of which are hereby incorporated by reference.

FIELD OF THE INVENTION

The present invention relates to a novel process for producing propylene chlorohydrin from water, chlorine and propylene.

PRIOR ART

Propylene chlorohydrin is an important compound as a raw material for producing propylene oxide.

The above propylene chlorohydrin is general produced by reacting propylene with chlorine in water.

However, in the above reaction, a side reaction occurs such that chlorine is added to the double bond of propylene to form propylene dichloride or that an ether is formed by a sequential reaction. Therefore, to prevent this, the reaction must be carried out by reducing the concentration of chlorine in the reaction system and the concentration of the formed propylene chlorohydrin (M M. P. Ferreo et al, Industrie Chmiqe Beige, vol. 19, page. 113, 1954).

The production of propylene chlorohydrin has been generally carried out industrially by using a reactor so called "chlorohydrin tower". That is, the following process has been widely employed using an annular reactor which comprises a gas-liquid separator having an exhaust gas extraction port and an output port for a propylene chlorohydrin aqueous solution in the upper portion and a U-shaped tube connected to the lower portion of the gas-liquid separator: propylene and at least part of an exhaust gas extracted from the exhaust gas extraction port are supplied from the bottom of the reactor to circulate a reaction solution with a gas lift formed by air bubbles of the exhaust gas as drive force, and part of a reaction solution containing the formed propylene chlorohydrin is extracted while chlorine is supplied into the lower reaches of the circulating solution little by little and make-up water is supplied to the reaction solution (Nikkan Kogyo Gisensho 14 Propylene-based Petrochemistry, pp. 106–110 published by Nikkan Kogyo Press Co., Ltd.).

However, as this process suppresses a side reaction as described above, the concentrations of chlorine and propylene chlorohydrin must be reduced to a low level, for example, 1 to 4 wt %.

Meanwhile, more and more importance is attached to effective use of oil resources due to decreasing oil resources and rising oil prices.

Therefore, the recovery of a propylene-containing gas having a propylene content of 70 to 96 vol % which is by-produced at the time of contact decomposition in the refining of oil is widely performed. It is desired that this propylene containing an impurity gas should be directly used without using labor and time for refining.

Further, in most chemical reaction processes using propylene as a raw material, including the above technology for producing propylene chlorohydrin, part of a gas containing propylene passing through a reactor is recycled to the reactor but the rest is often burnt as an exhaust gas. In general, the exhaust gas contains 10 to 70 vol % of propylene.

Therefore, if the exhaust gas can be effectively used, it will be extremely significant for the industry.

However, as the exhaust gas may have an extremely low content of propylene or vary in the content of propylene according to its supply source, it must be concentrated or refined to be utilized as a resource except when it is used as a fuel. However, the above treatment requires additional cost, thereby making it difficult to pay industrially.

To cope with this, the development of a process capable of making effective use of a gas having any content of propylene, particularly a low content of propylene as a raw material without concentrating it has been desired.

SUMMARY OF THE INVENTION

The inventors of the present invention have conducted studies with a view to developing a propylene chlorohydrin production process which is capable of producing propylene chlorohydrin from a gas having any content of propylene at a high utilization factor of propylene and a high selectivity and have found that the above object can be attained by the following simple process. That is, a composite reactor constructed by connecting in series a tubular reactor in which a reaction is carried out in a one-path co-current flow (to be referred to as "one-way flow" in claims and detailed description of the present application) and an annular reactor in which a reaction is carried out in a circulating flow is used, at least part of the supplied propylene and at least part of the supplied chlorine are reacted with each other in the tubular reactor, a reaction mixture fluid containing propylene chlorohydrin, propylene and/or chlorine discharged from the reactor is supplied to the annular reactor as a make-up medium (water) or part thereof in the annular reactor, the reaction is continued in the annular reactor by supplying propylene and/or chlorine as required to form a reaction solution having a desired content of propylene chlorohydrin, and the reaction solution is extracted from the annular reactor. Thus, the present invention has been accomplished based on this finding.

That is, the present invention relates to a process for producing propylene chlorohydrin, comprising the steps of supplying a propylene-containing gas to an aqueous solution of chlorine in a one-way flow reaction area using a reactor constructed by connecting the one-way flow reaction area and a circulating flow reaction area in series to carry out at least part of a propylene chlorohydrin forming reaction in the one-way flow reaction area in order to form a reaction mixture fluid containing propylene chlorohydrin and propylene and/or chlorine, supplying the reaction mixture fluid from the reaction area to the circulating flow reaction area as at least part of a make-up medium, as required, further supplying propylene and/or chlorine to the circulating flow reaction area to continue the reaction in order to obtain a reaction solution having a desired content of propylene chlorohydrin, and extracting part of the reaction solution.

One of the biggest features of the present invention is use of a composite reactor constructed by connecting a reaction area (one-way flow reaction area) in which a reaction is carried out in a one-way flow and a reaction area (circulating flow reaction area) in which a reaction is carried out in a circulating flow in series.

In the one-way flow reaction area, the aqueous solution of chlorine is first caused to run and a propylene-containing gas is supplied to the aqueous solution of chlorine in the passage of the solution to disperse the propylene-containing gas in the aqueous solution of chlorine as fine air bubbles so as to dissolve propylene in the solution and carry out a propylene chlorohydrin forming reaction. One of the important points in this one-way flow reaction area is that the supplied propylene should be dispersed and absorbed in the aqueous solution of chlorine swiftly. To this end, supply of the propylene gas through a porous plate or installation of at least one gas-liquid mixer, particularly a stationary mixer in the downstream area near a propylene-containing gas supply port of the passage of the aqueous solution of chlorine is effective means for dispersing the supplied propylene-containing gas swiftly, finely and uniformly.

Further, the tubular reactor used in the one-way flow reaction area is generally provided with a chlorine dissolution passage for dissolving chlorine in a water medium. In order to increase the dissolution speed of chlorine in the water medium in the passage, it is recommended to install a gas-liquid mixer, for example, a stationary mixer in the downstream area near the chlorine supply port of the passage.

Further, to increase the content of chlorine in the aqueous solution of chlorine (preferably the content of hypochlorous acid) is also effective because the amount of process water is reduced, the high selectivity of an object is obtained, and the reactor can be downsized. Therefore, while or after chlorine is dissolved in the water medium in the one-way flow area, an alkali is added to the aqueous solution so as to adjust its pH to a neutral range and not an alkali range, particularly 1 to 7, preferably 3 to 6 and then chlorine is reacted with propylene, which is preferred because propylene chlorohydrin can be obtained in a high concentration at a high selectivity of the object.

PH is desirably adjusted from an acidic range to the above pH range. When pH is adjusted from an alkaline range by introducing chlorine into the alkaline aqueous solution, the formation of a chlorate occurs and chlorine is wasted disadvantageously. When pH exceeds 7, the reaction rate for forming propylene chlorohydrin lowers considerably.

Thereafter, a reaction mixture fluid containing propylene chlorohydrin and propylene and/or chlorine discharged from the above one-way flow reaction area is supplied to the circulating flow reaction area as at least part of a make-up medium (water).

As the annular reactor used in the circulating flow reaction area is generally used an annular reactor of the same type as the so-called "chlorohydrin tower" which has been used for the production of propylene chlorohydrin. That is, it is an annular reactor which is composed of an upstream area, a downstream area and two upper and lower horizontal areas for connecting the two areas of the reaction solution and which has a chlorine supply port in the downstream area, a make-up medium supply port in the lower horizontal area or therearound, a propylene-containing gas supply port in a junction between the lower horizontal area and the upstream area, and a propylene chlorohydrin extraction port for extracting part of the reaction solution having a desired propylene chlorohydrin content, generally 2 to 10 wt % from the upper horizontal area (the upper horizontal area is generally a gas-liquid separator).

DETAILED DESCRIPTION OF THE PREFERRED EMBODIMENT

Figure 1:
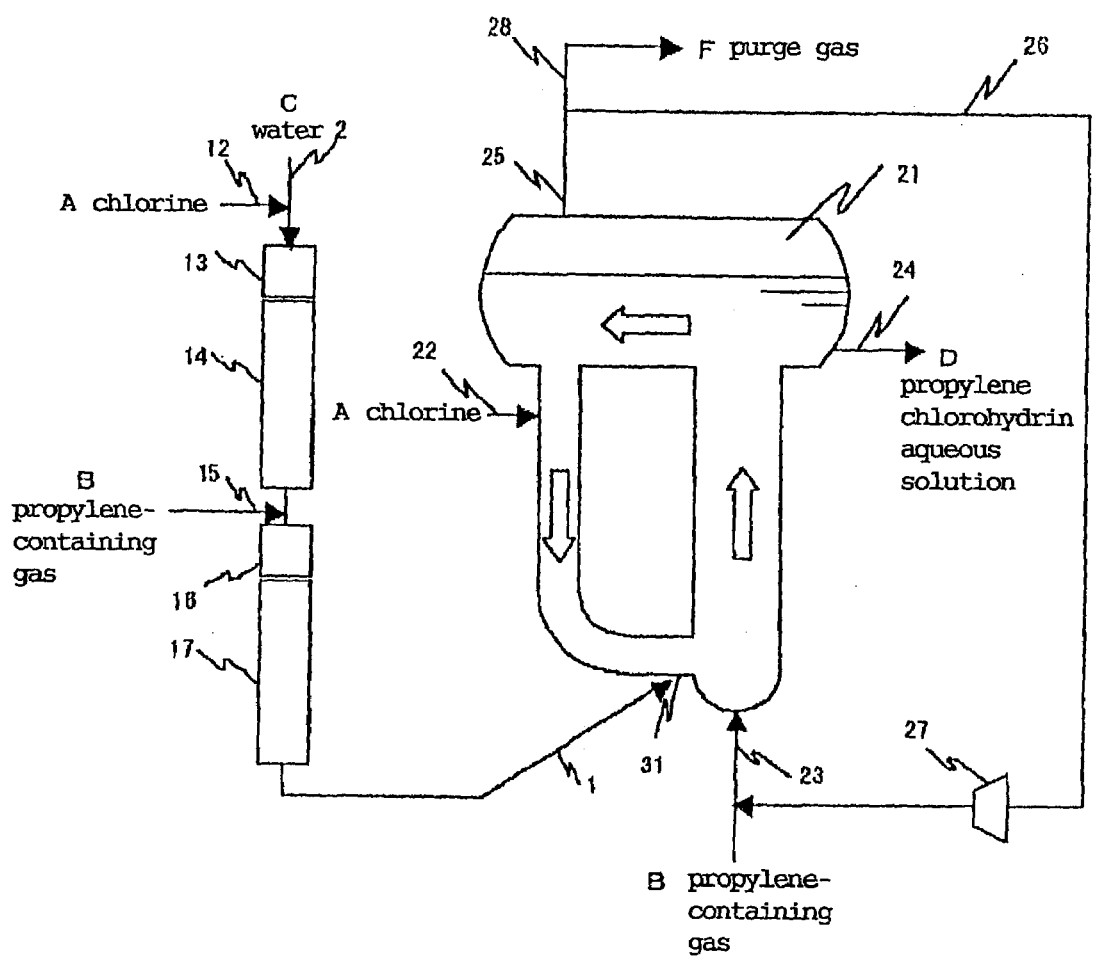
FIG. 1 is a conceptual diagram showing a typical example of an apparatus used in the process of the present invention.

Each element in each step of the process of the present invention will be described hereinunder.

(One-Way Flow Reaction Area)

In the present invention, a reaction between chorine and propylene in a water medium is first carried out in a one-way flow reaction area. That is, in the above area, a propylene-containing gas is supplied to the passage of an aqueous solution of chlorine from one site or a plurality of sites, a solution obtained after the mixing of the propylene-containing gas is let pass while it is prevented from flowing backward in the passage to be mixed with the solution at an upstream, a reaction for forming propylene chlorohydrin is caused to proceed in the passage, the content of propylene chlorohydrin is gradually increased, and a fluid obtained at the end of the one-way flow reaction area is introduced into a circulating flow reaction area.

The one-way flow reaction area is not particularly limited if it is a tubular reactor having a propylene-containing gas supply port or the like in a tubular passage having no circulation passage.

(Mixer)

In the above one-way flow reaction area, a mixer is preferably installed in the passage to mix the propylene-containing gas into the aqueous solution of chlorine running in the passage or to mix chlorine into a water medium as required. The mixer is particularly preferably a stationary mixer because it promotes the quick dissolution of the gas in the aqueous solution and an object can be obtained selectively.

Any known stationary mixer may be used. Specifically, ejectors, plate-like and cup-like collision board type stationary mixers, and Kenics, Sulzer, Etoflo, Tray Hi-mixer, Bran & Lubbe, N-form, Komax, Lightnin, Ross ISG and Prematechnik PMR type stationary mixers can be used. Mixers having high gas-liquid dispersion capability are preferred because they disperse chlorine or propylene-containing gas in an aqueous solution as fine air bubbles to accelerate the dissolution of the gas in the downstream passage. The above mixers include ejectors, plate-like and cup-like collision board type stationary mixers, and Kenics and Sulzer type stationary mixers.

Further, stationary mixers in which a flow of a fluid readily becomes an air bubble flow, plug flow or slag flow, particularly an air bubble flow after mixing are preferred, and ejectors, plate-like and cup-like collision board type stationary mixers and Sulzer type stationary mixers are particularly preferred.

In order to reduce the supply pressures of chlorine and a propylene-containing gas, the pressure difference between the inlet and outlet of the mixer is preferably small.

(Aqueous Solution of Chlorine and Chlorine)

In the present invention, the aqueous solution of chlorine which is caused to run in the passage of the one-way flow reaction area is not limited by its preparation process if the content of chlorine is adjusted to a value required for the reaction between chlorine and propylene. For example, it may be prepared using a known gas absorber so that before it is supplied to the tubular reactor, a dissolution tank is provided to blow chlorine into water in the tank. From an industrial point of view, a process for preparing the aqueous solution of chlorine by forming a passage for absorbing chlorine in the above one-way flow reaction area and supplying chlorine together with a water medium to be mixed together is preferred. In this case, a gas-liquid mixer is preferably installed in the passage at a chlorine supply site or a downstream near the site to effect the quick absorption of chlorine into water.

The content of chlorine in the prepared aqueous solution of chorine is reduced by a reaction between chlorine and the supplied propylene while it runs in the one-way flow reaction area. Then, chlorine is supplied along the passage of the tubular reactor to adjust the chlorine content of the aqueous solution of chlorine. In this case, after chlorine is supplied, a mixer is installed in the line to mix chlorine, thereby making it possible to dissolve chlorine in the aqueous solution of chlorine efficiently.

Supply of chlorine into the tubular reactor is carried out at an upstream of the mixer except when an ejector is used as the mixer. In the case of the ejector, as water for the process is used as a drive fluid for the ejector and chlorine is sucked as an extraction gas to be supplied, a supply port is formed in the inside of the ejector. The same can be said when a propylene-containing gas to be described hereinafter is supplied.

To supply chlorine in the circulating flow reaction area of the latter stage, it is generally directly supplied into the reaction area as a gas to adjust the content of chlorine in the aqueous solution of chlorine based on the amount of the reaction solution to be circulated. As will be described hereinafter, to supply a propylene-containing gas even in the circulating flow reaction area, it is recommended that an aqueous solution of chlorine should be prepared by supplying chlorine at an upstream of the propylene-containing gas.

In the present invention, chlorine may be gaseous purified chlorine obtained by liquefying and gasifying chlorine but use of unpurified gaseous chlorine having a purity of 99% and containing oxygen and water produced by electrolyzing an alkali metal chloride is economical and preferred.

The supply pressure of chlorine may be higher than the pressure of a solution flowing in the passage and high enough to supply gaseous chlorine. It is generally 1 KPaG to 700 KPaG.

The amount of chlorine is not particularly limited if it is lower than the solubility of chlorine which is determined by pressure and temperature. When it is too large, the amount of a by-product may become large and when it is too small, the time for obtaining the targeted content of chlorine is prolonged, resulting in the increased size of the reactor and triggering a side reaction.

Therefore, chlorine is preferably supplied to ensure that the content of chlorine in the passage of the reactor becomes 500 to 20,000 ppmw, particularly 800 to 15,000 ppmw.

In the one-way flow reaction area, one tubular reactor may have a plurality of sites for supplying chlorine, a plurality of sites for supplying a propylene-containing gas and a plurality of sites for mixing these, or a plurality of tubular reactors each having one site for supplying chlorine, one site for supplying a propylene-containing gas supply and one site for mixing these may be connected in series.

When a plurality of tubular reactors are connected in series in the one-way flow reaction area, it is also preferable embodiment that a pump is mounted in the connection portions to restore the supply pressure of the liquid.

The flowing direction of the fluid in the one-way flow reaction area may be horizontal, inclined or perpendicular. When the reactors are installed horizontally or at an angle, the fluid is apt to form a lamellar flow or wavy flow, thereby reducing the gas absorption coefficient and making it necessary to extend the length of the tube for gas absorption. Therefore, it is particularly preferred that they should be installed to form a descending flow in a perpendicular direction as much as possible because the area for forming an air bubble flow becomes large, the length of the whole apparatus can be reduced and the production scale can be easily increased.

(Water Medium)

In the present invention, although the supply pressure of the water medium or the aqueous solution of chlorine to the one-way flow reaction area is not particularly limited, the total of the restored pressure due to a height difference and a pressure loss of the mixer to be described hereinafter may be atmospheric pressure or higher to ensure the passage of the liquid. It is preferably 1 KPaG to 500 KPaG.

When the water medium to be supplied is used as drive force for an ejector as the mixer, it preferably has a pressure required for driving the ejector or higher to ensure complete gas absorption.

In the present invention, the flow rate of the water medium or the aqueous solution of chlorine to be supplied to the one-way flow reaction area is preferably adjusted to ensure that gas mixing capability is fully obtained and the fluid after it is mixed with a gas forms an air bubble flow, plug flow or slag flow, particularly preferably an air bubble flow.

The above preferred flow rate is not limited unconditionally but when a stationary mixer is used, the flow rate of the liquid introduced into the mixer is preferably 0.3 to 4 m/sec, more preferably 0.7 to 3 m/sec.

The above flow rate can be generally adjusted by the flow rate of the water medium or the aqueous solution of chlorine to be supplied to the one-way flow reaction area and the diameter of the tube of the tubular reactor. These concrete means are disclosed in Kagaku Kogyo Binran, the 5th edition, pp. 272–276 edited by Kagaku Kogakukai.

(Propylene-Containing Gas)

The propylene-containing gas used in the present invention contains propylene. When it contains an impurity gas, the impurity gas is not particularly limited if it does not prevent the reaction of the present invention. The gas contains propylene in an amount of preferably 5 to 100 vol %, more preferably 10 to 100 vol %, much more preferably 12 to 100 vol %. A gas whose propylene content has been adjusted by mixing an exhaust gas having a low content of propylene with a gas having a high content of propylene may also be used.

Illustrative examples of the propylene-containing gas include an exhaust gas having a propylene content of 10 to 70 vol % discharged during the production of propylene chlorohydrin, an FCC recovered propylene-containing gas having a propylene content of 70 to 96 vol % recovered from a by-produced gas during contact decomposition for oil refining, a propylene-containing gas having a propylene content of 92 to 100 vol % produced from the cracking of naphtha, and an exhaust gas having a propylene content of 10 to 70 vol % discharged during the production of isopropyl alcohol, coumene, acetone, acrolein, acrylic acid, acetonitrile, allyl chloride or polypropylene. Particularly preferred are an exhaust gas having a propylene content of 10 to 70 vol % discharged during the production of propylene chlorohydrin, an FCC recovered propylene-containing gas having a propylene content of 70 to 96 vol % recovered from a by-produced gas during contact decomposition for oil refining, and a propylene-containing gas having a propylene content of 92 to 100 vol % produced from the cracking of naphtha.

A component other than propylene contained in the propylene-containing gas must be an inert gas which does not prevent a reaction during the production of propylene chlorohydrin and preferably does not have an ill effect on the purification of propylene oxide which is subsequently produced from the object. Specific examples of the component include hydrocarbons such as butane, isobutane, propane, cyclopropane, ethane and methane, nitrogen, hydrogen, oxygen, carbon monoxide and carbon dioxide. When oxygen is contained, propane, nitrogen or the like is preferably added for safety's sake to prevent an exhaust gas discharged from the circulating flow reaction area connected to the latter stage of the one-way flow reaction area to be described hereinafter from reaching an explosive range.

The supply pressure of the above propylene-containing gas will suffice for the supply of the propylene-containing gas if it is higher than the pressure of the fluid flowing in the tubular reactor and the annular reactor. It is preferably 1 KPaG to 700 KPaG.

When the supply of the propylene-containing gas is too large, the amount of an unreacted product becomes large and when the supply is too small, the amount of a by-product becomes large. Therefore, it is preferably 0.9 to 2 mols, particularly preferably 1 to 1.5 mols in terms of propylene pure content based on 1 mol of chlorine supplied.

The supply position of the propylene-containing gas is preferably a position where the supplied chlorine dissolves completely when chlorine is supplied into the passage of the tubular reactor in the one-way flow reaction area of the former stage or the annular reactor in the circulating flow reaction area of the latter stage. The position may be determined by experiments in advance. To ensure the complete dissolution of chlorine, a chlorine residence time of 4 seconds or more is preferably ensured after chlorine is mixed.

After the propylene-containing gas is mixed, a residence time of 10 seconds or more is preferably ensured to increase the reaction rate between the dissolved chlorine and propylene.

(Adjustment of pH of Aqueous Solution of Chlorine)

In the present invention, addition of an alkali to the aqueous solution of chlorine running in the passage of the tubular reactor to a pH of not more than 7 is preferred because the selectivity of the obtained propylene chlorohydrin becomes high.

That is, when chlorine is dissolved in water, it reacts with water to cause a reversible reaction for forming hypochlorous acid and hydrochloric acid. In the process of the present invention, by supplying an alkali to chlorine dissolved in water, the formed hydrochloric acid is selectively neutralized to form a salt because its dissociation constant is large (hypochlorous acid: $4 \times 10^{-8}$, hydrochloric acid: $1 \times 10^{-1}$). As a result, the above reversible reaction for forming hypochlorous acid is promoted, thereby making it possible to obtain an aqueous solution having an extremely low content of chlorine and a high content of hypochlorous acid. It is assumed that the formation of a by-product by the addition of chlorine to the double bond of propylene can be also suppressed by supplying propylene to a flow of the above solution in the present invention, thereby further increasing the selectivity of propylene chlorohydrin of interest.

The alkali to be supplied in order to adjust the above pH is not limited to a particular type but preferably an alkali metal hydroxide such as lithium hydroxide, sodium hydroxide or potassium hydroxide, alkali earth metal hydroxide such as magnesium hydroxide, calcium hydroxide or barium hydroxide, alkali metal carbonate such as sodium carbonate, sodium bicarbonate or potassium carbonate, or alkali earth metal carbonate such as magnesium carbonate or calcium carbonate. Calcium hydroxide is particularly preferred because it is easily acquired.

The amount of the alkali must be such that pH of the aqueous solution of chlorine should not exceed 7 as described above. The supply of the alkali is preferably controlled to ensure that the pH should fall within a range of 1 to 7, particularly 3 to 6 because a solution having a low content of chlorine and a high content of hypochlorous acid can be obtained.

The method of supplying the above alkali is not particularly limited but the alkali is preferably supplied continuously as an aqueous solution or slurry having an alkali content of 1 to 40 wt %. A pH controller comprising a valve for controlling the flow rate of the alkali based on a signal from a pH detector for detecting the fluid in the one-way flow reaction area is preferably used to control pH.

The addition of the alkali is preferably carried out by installing a stationary mixer in the passage at a downstream of an alkali supply port.

Since chlorine dissolves in water in an extremely short period of time by adding the alkali, the residence time of chlorine after mixing can be shortened. In general, a residence time of 2 seconds or more suffices.

(Connection Between Tubular Reactor and Annular Reactor)

The important features of the present invention are that a reaction is carried out in one path by supplying the propylene-containing gas to the aqueous solution of chlorine in the one-way flow reaction area and then the reaction mixture fluid is introduced into the annular reactor connected to the rear end of the tubular reactor to continue the reaction until the targeted concentration of propylene chlorohydrin is obtained while the reaction mixture fluid is circulated in the circulating flow reaction area and that an unreacted gas and the aqueous solution of the reaction product are separated from each other and taken out.

Although the reaction rates in the one-way flow reaction area and the circulating flow reaction area are not particularly limited in the present invention, 50% or more of the propylene pure content supplied from the one-way flow reaction area is preferably reacted in the one-way flow reaction area. It is particularly preferred that the reaction rate of propylene in the reaction areas should be maintained at a higher level as the content of propylene in the propylene-containing gas used increases because propylene chlorohydrin can be obtained in a higher concentration at higher selectivity. Chlorine supplied into the one-way flow reaction area does not need to be consumed completely in the one-way flow reaction area.

As a matter of course, the propylene-containing gas and/or chlorine gas (or an aqueous solution of chlorine) can be newly supplied to the circulating flow reaction area as required.

In general, the propylene-containing gas must be supplied at a position for providing a drive function for helping the circulation of the fluid in the annular reactor. When chlorine is to be supplied, it should be supplied at an upstream of the propylene-containing gas supply port. When both chlorine and the propylene-containing gas are to be supplied to the annular reactor, the supply of chlorine, the introduction of the reaction mixture fluid from the one-way flow reaction area and the supply of the propylene-containing gas are carried out in the order named from an upstream side in the flow direction of the circulating fluid. Thereby, the dissolution of chlorine in the annular reactor is performed smoothly and a side-reaction can be suppressed.

More specifically, when a reactor making use of a gas lift to be described hereinafter is selected, it is preferred that chlorine should be supplied to the downstream area of the circulating fluid in the annular reactor, the reaction mixture fluid from the one-way flow reaction area and the water medium added as required should be merged near the lower part of the area, and the propylene-containing gas should be supplied near a site where they turn into an ascending flow.

The merging angle of the fluid supplied from the above one-way flow reaction area is not particularly limited but preferably an angle which does not prevent a flow of the circulating fluid. The angle between the flowing directions of the both fluids is an acute angle of preferably 90° or less, more preferably 60° or less, and further more preferably 45° or less.

In the present invention, examples of the annular reactor for forming a preferred circulating flow reaction area are given below: (1) one employing the prior art method, that is, so-called "chlorohydrin tower" having a gas-liquid separator with an exhaust gas extraction port and a propylene chlorohydrin output port in the upper portion and a U-shaped tube connected to the lower portion of the separator, in which a propylene-containing gas and at least part of an exhaust gas extracted from the exhaust gas extraction port are supplied from below and chlorine is supplied into the area of a descending flow little by little while a reaction solution is circulated using a gas lift of air bubbles formed by these gases as drive force, and water is supplied to the reaction solution to take out propylene chlorohydrin, and (2) one having a chlorine supply port and a propylene supply port in the passage and comprising a tubular reactor having a mixer at a downstream of each of the supply ports and a gas-liquid separator connected to an opening at the rear end of the tubular reactor, in which a reaction solution separated by the gas-liquid separator is supplied to an opening at the front end of the tubular reactor by a circulation pump to form a circulating system. The former reactor called "chlorohydrin tower" is particularly preferred because it can improve the utilization factor of propylene stably.

One to three chlorohydrin towers are connected in series to contact the propylene-containing gas to a counterflow of the exhaust gas in order to enhance the utilization factor of propylene and the selectivity of propylene chlorohydrin, thereby making it possible to increase the content of propylene chlorohydrin.

(Amounts of Loads in One-Way Flow Reaction Area and Circulating Flow Reaction Area)

In the present invention, as for the ratio of the supply of chlorine and the supply of propylene to the one-way flow reaction area and the circulating flow reaction area, any ratio can be selected and may be determined based on which reactor is mainly used.

In general, when selectivity is to be improved, the amounts of raw materials to be supplied to the one-way flow reaction area of the former stage may be increased and when the utilization factor of propylene is to be enhanced, the amounts of raw materials to be supplied to the circulating flow reaction area of the latter stage may be increased.

The exhaust gas to be discharged from the circulating flow reaction area of the latter stage is partially discharged as a purge gas and partially recycled to the propylene-containing gas supply port of the reactor and as a propylene-containing gas to be supplied to the one-way flow reaction area to produce propylene chlorohydrin. Thus, the utilization factor of propylene can be enhanced.

A small amount of the residual propylene contained in the purge gas to be discharged to the outside of the system can be taken out as an aqueous solution of propylene chlorohydrin by the method disclosed by JP-A 2000-347514 or the like.

(Reaction Temperature and the Like)

In the present invention, since the selectivity of propylene chlorohydrin of interest is apt to lower when the reaction temperature is too high, the temperature of the obtained aqueous solution of propylene chlorohydrin is preferably adjusted to 80° C. or less. The method of adjusting the temperature is not particularly limited but the method of adjusting the temperature of the water medium or the aqueous solution of chlorine to be supplied to the one-way flow reaction area is preferred. That is, the temperature of the water medium or the aqueous solution of chlorine to be supplied to the one-way flow reaction area is preferably 70° C. or less, particularly preferably 0 to 60° C. in consideration of the heat of a reaction for forming propylene chlorohydrin.

Thus, a chlorohydrin can be produced in accordance with a simple process stably at a high selectivity of the object and a high utilization factor of propylene by passing chlorine, a propylene-containing gas having any content of propylene selected from a wide range and water through the one-way flow reaction area and the circulating flow reaction area.

The material of the composite reactor of the present invention is not particularly limited if it does not cause a problem such as corrosion except the nozzle of the chlorine support port. For example, it is a corrosion resistant metal material such as titanium lined with a polymer material such as polytetrafluoroethylene. The nozzle of the chlorine support port is preferably made from a polymer material such as polytetrafluoroethylene because when titanium is used, it reacts with chlorine.

The aqueous solution of propylene chlorohydrin obtained by the process of the present invention can be used directly as a raw material for producing propylene oxide.

A typical embodiment of the above process will be described hereinbelow with reference to FIGS. 1 and 2.

FIG. 1 shows a typical embodiment of the present invention.

That is, in the embodiment shown in FIG. 1, water C is supplied into the apparatus from a supply port 2 and mixed with chlorine supplied into a stationary mixer 13 from a chlorine gas supply port 12 to disperse chlorine A into water as fine air bubbles.

Thereafter, water mixed with the above chlorine A dissolves chlorine in the passage 14 of a one-way flow reaction area and dissolution is completed before it reaches a propylene-containing gas supply port 15 to prepare an aqueous solution of chlorine.

Then, a propylene-containing gas B is supplied to the aqueous solution of chlorine from the gas supply port 15.

The supplied propylene-containing gas is mixed with the aqueous solution of chlorine in a stationary mixer 16 to disperse the propylene-containing gas into the aqueous solution of chlorine as fine air bubbles.

In a passage 17 after the mixer, the formation of propylene chlorohydrin and hydrogen chloride proceeds by a reaction of propylene, chlorine and water to produce a gas-liquid reaction mixture fluid comprising an aqueous solution containing propylene chlorohydrin, a component other than propylene contained in the propylene-containing gas, unreacted propylene, hydrochloric acid and, according to circumstances, chlorine.

Meanwhile, chlorine A is supplied into a circulating flow reactor 21 from a chlorine supply port 22, the dissolution of a chlorine gas is promoted by the function of a circulating reaction solution, and almost all the chlorine is dissolved into the reaction solution before it reaches a water medium supply port 31.

Then, this aqueous solution of chlorine and the reaction mixture fluid guided over a line 1 from the above one-way flow reaction area merge at the position of the water medium supply port 31.

At this point, a circulating flow can be made smoother by adjusting the merging angle of the both fluids at an acute angle of 60° or less.

Then, a propylene-containing gas from a propylene-containing gas supply port 23 below the circulating flow reaction area 21 and a gas obtained by increasing the pressure of part of an exhaust gas extracted from the exhaust gas extraction port 25 of the gas-phase portion of a gas-liquid separator existent above the annular reaction area 21 by a pressure pump 27 through a line 26 are supplied as reaction solution circulation drive sources.

While a newly added propylene-containing gas and a propylene chlorohydrin-containing gas-liquid mixed fluid comprising a component other than propylene contained in the above propylene-containing gas and unreacted propylene rise in the ascending flow portion of the circulating flow reaction area 21, the propylene component reacts with the aqueous solution of chlorine to further form propylene chlorohydrin, thereby increasing the content of propylene chlorohydrin in the reaction solution.

Part of the exhaust gas extracted from the exhaust gas extraction port 25 is discharged from a purge gas output port 28 as a purge gas. This purge gas can be burnt as it is and a propylene collection unit can be installed in the latter stage.

The formed propylene chlorohydrin is taken out as a propylene chlorohydrin aqueous solution D from a propylene chlorohydrin aqueous solution output port 24.

Figure 2:
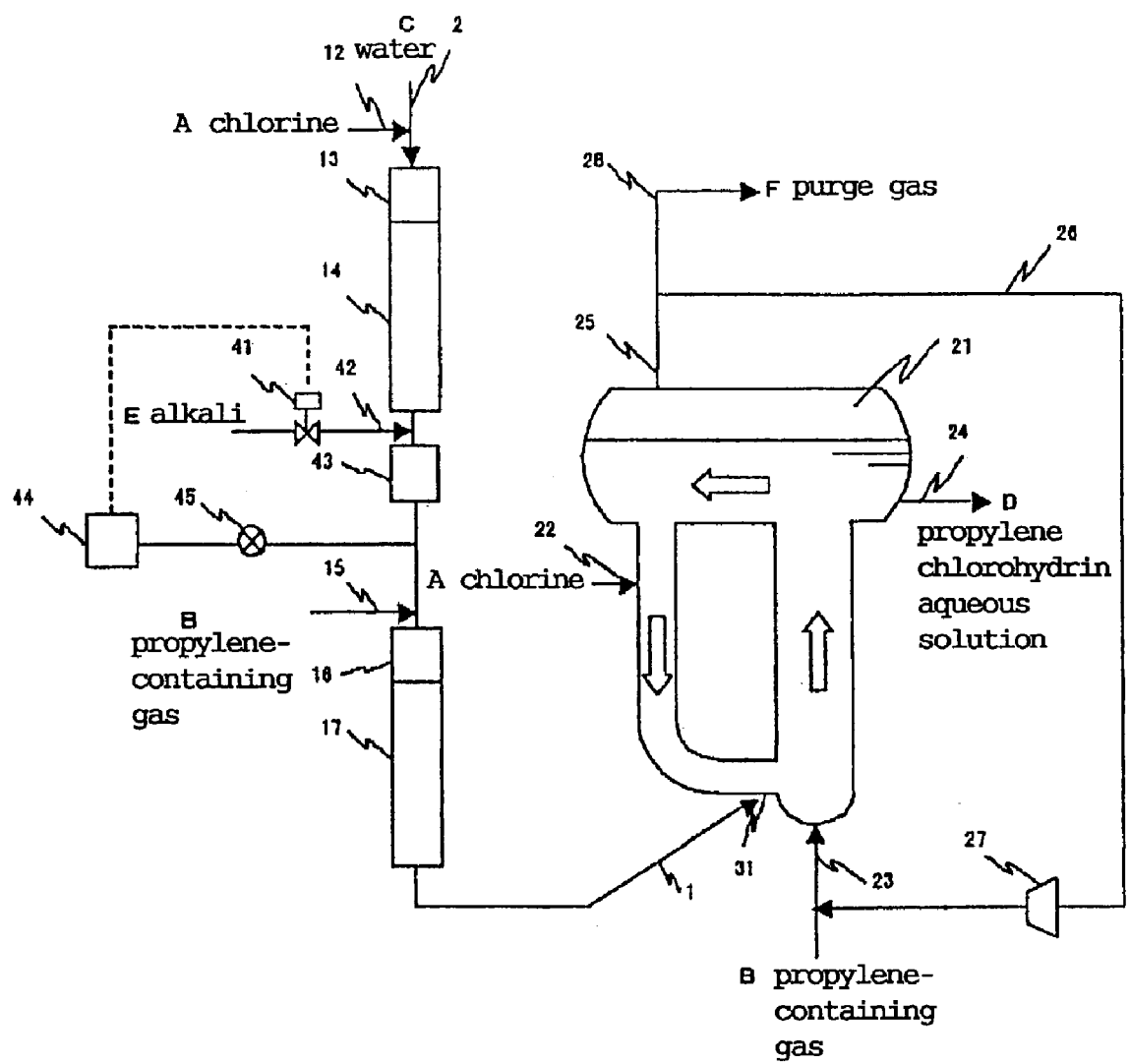
FIG. 2 is a conceptual diagram showing another typical example of an apparatus used in the process of the present invention.

FIG. 2 shows another typical embodiment of the present invention.

The apparatus shown in FIG. 2 is a composite reactor showing another typical embodiment of the present invention. That is, it shows an embodiment that pH of the aqueous solution of chlorine is adjusted by adding an alkali.

In the apparatus of FIG. 2, an alkali supply port 42 having a control valve 41 for adding an alkaline aqueous solution E is installed in a passage right after a passage 14 for preparing an aqueous solution of chlorine while pH of the aqueous solution is controlled, and a stationary mixer 43, a pH detector 45 and an arithmetic unit 44 for converting a signal from the pH detector 45 into a signal for controlling the control valve 41 are arranged at a downstream of the alkali supply port 42 to control the control valve 41.

As understood from the above description, according to the present invention, propylene chlorohydrin can be produced from a propylene-containing gas having any propylene content selected from a wide range industrially advantageously at a high selectivity of the object and a high utilization factor of propylene in accordance with the process of producing propylene chlorohydrin by reacting chlorine with propylene in water.

Therefore, the industrial value of the present invention is extremely high.

EXAMPLES

The following examples are provided for the purpose of further illustrating the present invention but are in no way to be taken as limiting.

Example 1

The apparatus shown in FIG. 1 was used. That is, a tubular reactor having an inner diameter of 27.6 mm and a pipe length of 20 m after mixing a propylene-containing gas and provided with a chlorine supply port, a propylene-containing gas supply port and a cup collision board type mixer shown in FIG. 1 of JP-A 9-29977 for mixing chlorine with a propylene-containing gas was used as a tubular reactor having a one-way flow reaction area of a first stage. A composite reactor which was an annular reactor having an expanded upper portion as a gas-liquid separation area, an upstream area inner diameter of 500 mm, a height of 5 m, a downstream area inner diameter of 300 mm and a height of 5 m was installed at the end of a downstream of the above reactor as a circulating flow reactor of a second stage in order to merge the reaction mixture fluid supplied to the circulating flow reaction area from the one-way flow reaction area with a fluid running in the circulating flow reaction area at an acute angle of 30° between the flowing directions of the both fluids.

Water was supplied from the proximal end portion of the tubular reactor at a rate of 3.2 m$^3$/hr, chlorine was supplied at a rate of 5.25 Nm$^3$/hr, and a propylene-containing gas having a propylene content of 95% was supplied at a rate of 5.80 Nm$^3$/hr to carry out a propylene chlorohydrin forming reaction as the first stage by setting the temperature of the first-stage outlet to 25° C. in order to obtain a reaction mixture fluid. The solution of the reaction mixture fluid flowing in the first-stage reactor contained 50 ppm of effective chlorine derived from chlorine and hypochlorous acid and 0.02 wt % of a by-product such as propylene dichloride.

Thereafter, chlorine was supplied to a reaction solution through the chlorine support port at a rate of 12.5 Nm$^3$/hr in the annular reactor through which the reaction solution was circulated by a gas lift of the propylene-containing gas to be merged with the above reaction mixture fluid from the above tubular reactor, a circulation gas having a flow rate of 8.8 Nm$^3$/hr out of a propylene-containing gas having a propylene content of 95% from the propylene-containing gas supply port and an exhaust gas extracted from the exhaust gas extraction port of a gas-liquid separation area was supplied to carry out a second-stage chlorohydrination reaction.

An aqueous solution containing 2.2 wt % of propylene chlorohydrin was obtained from the output port of the reaction system at a rate of 3.3 Nm$^3$/hr and a purge gas was obtained at a rate of 1.0 Nm$^3$/hr.

When the obtained aqueous solution and gas were analyzed, the selectivity of propylene chlorohydrin was 95.5% and the reaction rate of propylene was 99.5%. The operation conditions and results are shown in Table 1.

Examples 2 to 3

The procedure of Example 1 was repeated except that the content and supply rates of chlorine and the propylene-containing gas were changed as shown in Table 1. The results are shown in Table 1.

Examples 4 to 6

The procedure of Example 1 was repeated except that 17% of milk of lime as an alkali was supplied from the alkali supply port to the apparatus shown in FIG. 2, that is, an apparatus having a unit for adjusting pH of the aqueous solution of chlorine by adding an alkali at a downstream of the chlorine supply port in the tubular reactor area to control pH to 4 in order to carry out a chlorohydrination reaction under conditions shown in Table 1. The results are shown in Table 1.

Comparative Examples 1 and 2

Figure 3:
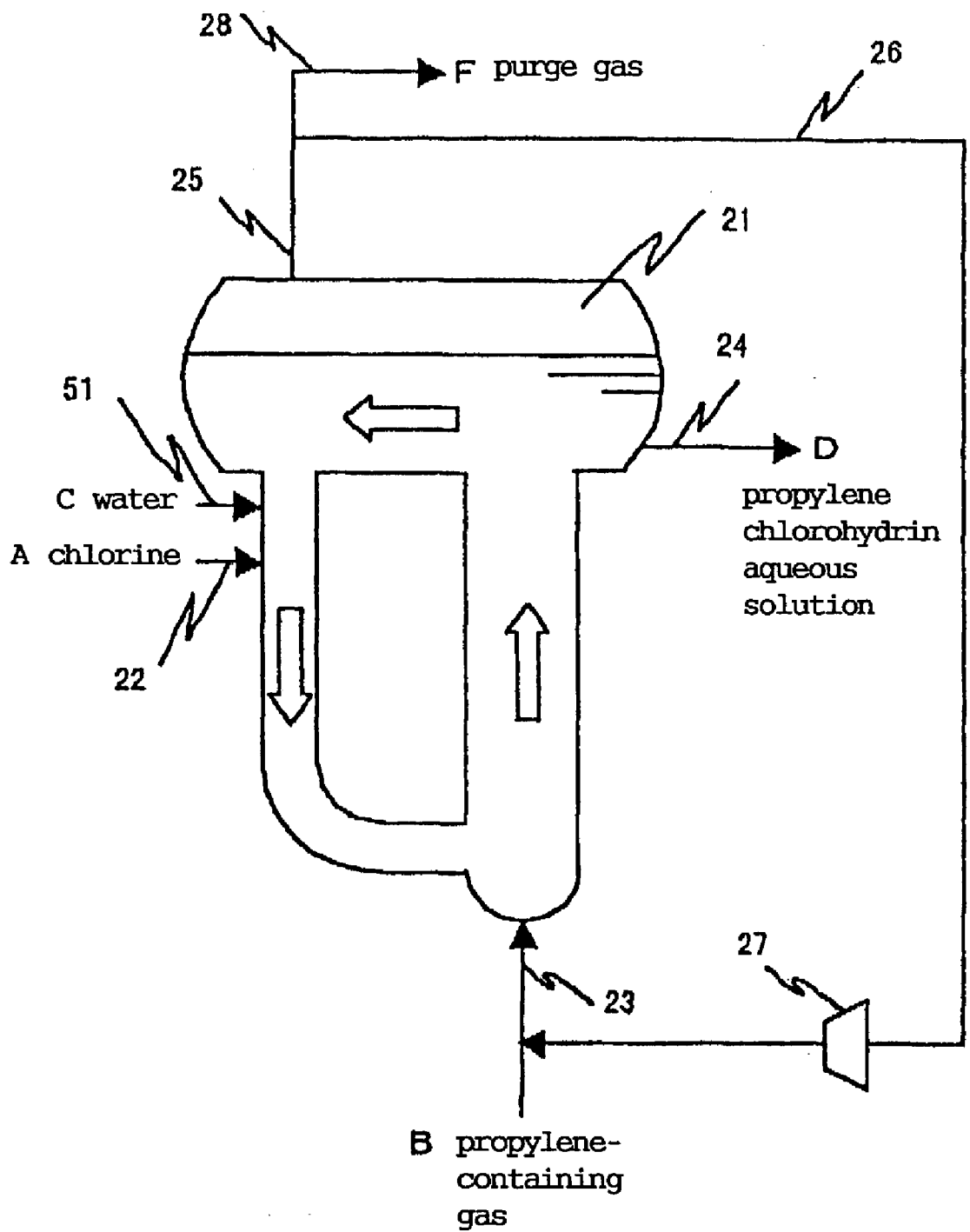
FIG. 3 is a conceptual diagram showing a typical example of an apparatus used in Comparative Example.

A chlorination reaction was carried out by supplying water from the chlorine supply port of the apparatus shown in FIG. 3, that is, an apparatus consisting of only an annular reaction area under conditions shown in Table 1 (see FIG. 3). The results are shown in Table 1.

TABLE 1

| | Conditions | | | | | | | | |
|---|---|---|---|---|---|---|---|---|---|
| | Tubular reactor area | | | | | Annular reactor area | | | |
| | | | | Proplyene-containing gas | | | Propylene-containing gas | | Circulating |
| Example | Supply of Water (m³/h) | Supply of chlorine (Nm³/h) | Control of pH after supply of milk of line | Content of propylene (Volume %) | Supply of proplyene-containing gas (Nm³/h) | Supply of chlorine (Nm³/h) | Content of propylene (Volume %) | Supply of propylene-containing gas (Nm³/h) | gas Amount of circulating gas (Nm³/h) |
| Ex. 1 | 3.2 | 5.25 | | 95.0 | 5.80 | 12.5 | 95.0 | 12.9 | 8.8 |
| Ex. 2 | 3.2 | 0.88 | | 15.0 | 7.05 | 12.5 | 95.0 | 13.0 | 8.8 |
| Ex. 3 | 3.2 | 3.87 | | 70.0 | 5.80 | 9.3 | 70.0 | 13.0 | 8.8 |
| Ex. 4 | 3.2 | 5.25 | 4.0 | 95.0 | 5.80 | 12.5 | 95.0 | 12.9 | 8.8 |
| Ex. 5 | 3.2 | 0.83 | 3.1 | 15.0 | 5.80 | 12.5 | 95.0 | 13.0 | 8.8 |
| Ex. 6 | 3.2 | 3.87 | 4.7 | 70.0 | 5.80 | 9.3 | 70.0 | 13.0 | 8.8 |
| C. Ex. 1 | 3.2 | | | | | 12.5 | 95.0 | 13.2 | 8.8 |
| C. Ex. 2 | 3.2 | | | | | 9.3 | 70.0 | 13.3 | 8.8 |

| | Results | | | |
|---|---|---|---|---|
| Example | Selectivity of propylene chlorohydrin (%) | Reaction rate of propylene (%) | Propylene content of purge gas (Volume %) | Flow of rate of purge gas (Nm³/h) |
| Ex. 1 | 96.5 | 99.5 | 8.7 | 1.0 |
| Ex. 2 | 96.9 | 99.0 | 2.0 | 6.8 |
| Ex. 3 | 97.0 | 98.0 | 4.5 | 5.9 |
| Ex. 4 | 97.0 | 99.6 | 7.1 | 1.0 |
| Ex. 5 | 97.5 | 99.2 | 1.9 | 5.7 |
| Ex. 6 | 97.4 | 98.2 | 4.0 | 5.9 |
| C. Ex. 1 | 95.1 | 97.8 | 29.5 | 0.9 |
| C. Ex. 2 | 95.8 | 94.5 | 11.4 | 4.5 |

Ex. = Example
C. Ex. = Comparative Example

What is claimed is:

1. A process of producing propylene chlorohydrin, comprising the steps of:
   supplying a propylene-containing gas to an aqueous solution of chlorine in the one-way flow reaction area of a reactor having the one-way flow reaction area and a circulating flow reaction area which are connected in series to carry out at least part of a propylene chlorohydrin forming reaction in order to form a reaction mixture fluid containing propylene chlorohydrin and propylene and/or chlorine;
   supplying the reaction mixture fluid from the reaction area to the circulating flow reaction area as at least part of a make-up medium;
   as required, further supplying a propylene-containing gas and/or chlorine to the circulating flow reaction area to continue the reaction in order to obtain a reaction solution having a desired content of propylene chlorohydrin; and extracting part of the reaction solution.

2. The process of claim 1, wherein an alkali is added to control pH of the aqueous solution of chlorine to a range of 1 to 7 in the one-way flow reaction area while or after chlorine is dissolved in a water medium.

3. The process of claim 1 or 2, wherein the reaction mixture fluid supplied from the one-way flow reaction area to the circulating flow reaction area is merged with a circulating solution running in the circulating flow reaction area at an acute angle of 60° or less between the flowing directions of the both fluids.

4. The process of claims 1, wherein a tubular reactor having a mixer in the passage of the aqueous solution of chlorine after the supply of the propylene-containing gas in the one-way flow reaction area is used.

5. The process of claims 1, wherein the propylene content of the propylene-containing gas is 10 vol % or more.

6. The process of claims 1, wherein a composite reactor having a tubular reactor and an annular reactor connected in series is used.

* * * * *